United States Patent [19]
Efange et al.

[11] Patent Number: 5,554,752
[45] Date of Patent: Sep. 10, 1996

[54] SPIROVESAMICOLS

[75] Inventors: Simon M. N. Efange, Plymouth, Minn.; Stanley M. Parsons, Santa Barbara, Calif.

[73] Assignee: Regents of the University of Minnesota, Minneapolis, Minn.

[21] Appl. No.: 405,491

[22] Filed: Mar. 14, 1995

Related U.S. Application Data

[62] Division of Ser. No. 131,887, Oct. 5, 1993, Pat. No. 5,457,207.

[51] Int. Cl.$^6$ .................................................. C07D 401/04
[52] U.S. Cl. ........................................... 546/17; 546/191
[58] Field of Search ........................ 546/17, 191, 44, 546/150, 187, 206, 240, 241; 544/392; 514/278, 282, 307, 316, 317

[56] References Cited

U.S. PATENT DOCUMENTS

| | | | |
|---|---|---|---|
| 3,654,287 | 4/1972 | Dykstra | 546/17 |
| 3,666,764 | 5/1972 | Campbell et al. | 546/17 |
| 4,593,037 | 6/1986 | Sarges | 514/317 |
| 4,595,535 | 6/1986 | Vlattas | 514/220 |
| 5,023,266 | 6/1991 | Langer et al. | 514/317 |
| 5,219,860 | 6/1993 | Chambers et al. | 514/278 |
| 5,324,733 | 6/1994 | Billington et al. | 514/278 |
| 5,464,788 | 11/1995 | Bock et al. | 514/252 |

OTHER PUBLICATIONS

"Nonsymmetrical Bipiperidyls As Inhibitors of Vesicular Acetylcholine Storage", pp. 985–989, from *Journal of Medicinal Chemistry*, vol. 93, 1993.

"The Neuromuscular Blocking Action of 2–(4–Phenylpiperidino) Cyclohexanol (AH 5183)", Brittain et al. 1969.

"The Vesicular Acetylcholine Transport System", Marshall and Parsons, 1987.

"Fractional Vesamicol Receptor Occupancy and Acetylcholine Active Transport Inhibition in Synaptic Vesicles", Kaufmann et al. 1988.

"Fractional Vesamicol Receptor Occupancy and Acetylcholine Active Transport Inhibition in Synaptic Vesicles", Kaufmann 1988.

"Synthesis, In Vitro Acetylcholine–Storage–Blocking Activities, and Biological Properties of Derivatives and Anaogues of Trans–2–(4–Phenylpiperidino)Cyclohexanol(Vesamicol)", Rogers et al. 1989.

"Acyclic Analogues of 2–4(Phenylpiperindino)Cyclohexanol(Vesamicol): Conformationally Mobile Inhibitors of Vesicular Acetylcholine Transport", Efange et al. 1991.

"Antiphyshotic Agents", Carl Kaiser et al., Burger's Medicinal Chemistry, Fourth Edition, Part III. 1987.

*Primary Examiner*—Ceila Chang
*Attorney, Agent, or Firm*—Vidas, Arrett & Steinkraus

[57] ABSTRACT

The compounds are vesamicol (hydroxylated phencyclidine (PCP) isomer trans-2-(4-phenyl-piperidino)cyclohexanol) derivatives with anticholinergic properties termed herein "spirovesamicols" which are spirofused piperidines. The compounds bind to the vesamicol receptor, a site on the cholinergic synaptic vesicle, which is associated with the vesicular transporter of acetylcholine.

1 Claim, 4 Drawing Sheets

1a  R = H; Vesamicol
1b  R = Cl; Chlorovesamicol
1c  R = NO₂; Nitrovesamicol

2a

2b

3

4

5a  R = R' = H
5b  R = CH₃; R' = H
5c  R = H; R' = CH₃

6a

6b

7a

7b

*Fig. 11*  *Fig. 12*  *Fig. 13*
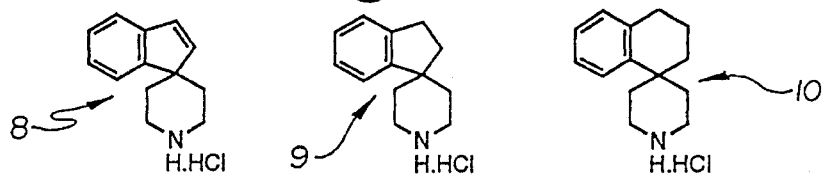
*Fig. 14*
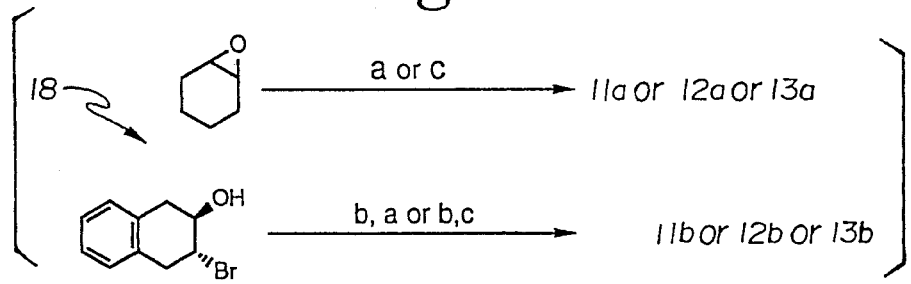
*Fig. 15*
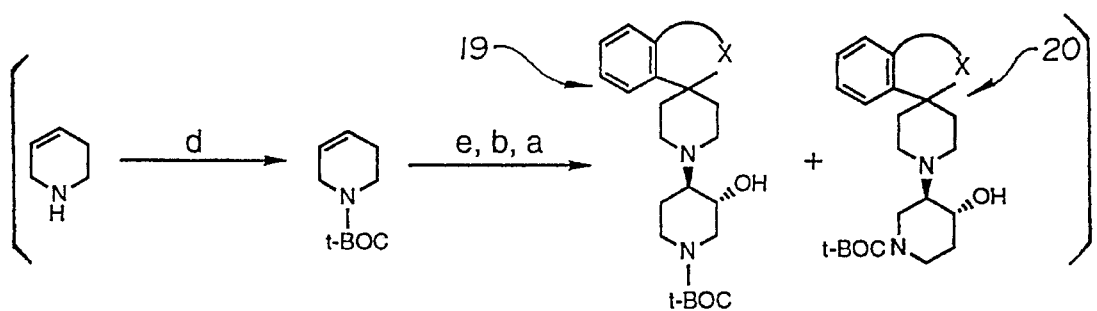
*Fig. 16*
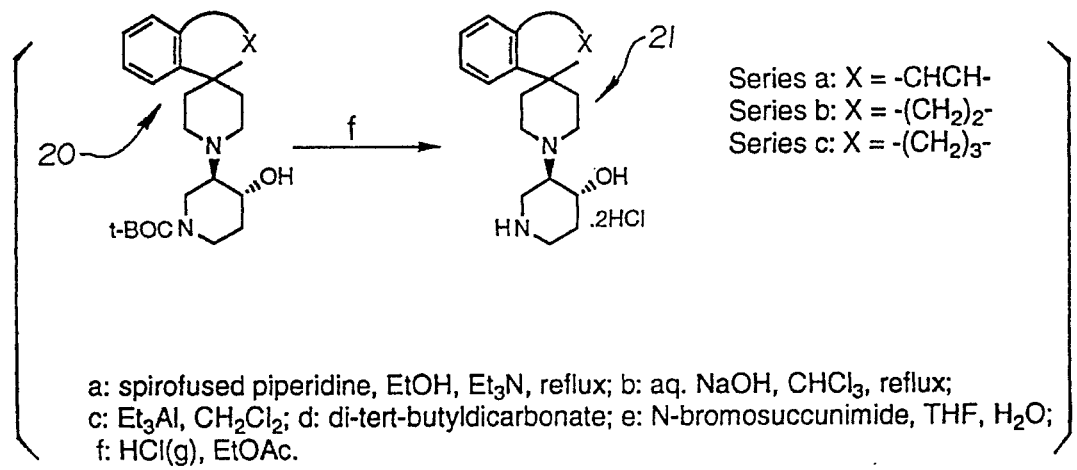
Series a: X = -CHCH-
Series b: X = -(CH$_2$)$_2$-
Series c: X = -(CH$_2$)$_3$-
a: spirofused piperidine, EtOH, Et$_3$N, reflux; b: aq. NaOH, CHCl$_3$, reflux;
c: Et$_3$Al, CH$_2$Cl$_2$; d: di-tert-butyldicarbonate; e: N-bromosuccunimide, THF, H$_2$O;
f: HCl(g), EtOAc.

a: LiN(SiMe$_3$)$_2$, BocN(CH$_2$CH$_2$Cl)$_2$, 0°C; b: HCl(g), EtOAc;
c: 1,4-dihydronaphthalene oxide, EtOH, Et3N, reflux;
d: 1,4-dihydronaphthalene oxide, Et$_3$Al, CH$_2$Cl$_2$.

Series c: R = o-I
Series d: R = m-I
Series e: R = p-I
Series f: R = p-F

SPIROVESAMICOLS

STATEMENT AS TO RIGHTS

This invention was made with government support under grant NS-28711 awarded by the National Institute of Health. The Government has certain rights in this invention.

CROSS-REFERENCE TO RELATED APPLICATIONS

This application is a division of Ser. No. 08/131,887 filed Oct. 5, 1993 now U.S. Pat. No 5,457,207.

BACKGROUND OF THE INVENTION

1. Field of the Invention

This invention relates to vesamicol derivatives that have anticholinergic properties.

2. Description of the Related Art

Cholinergic neurotransmission is comprised of several functional units. These include: 1) sequestration, by presynaptic cholinergic terminals, of choline, the precursor for the synthesis of acetylcholine (ACh); 2) the synthesis of ACh catalyzed by choline acetyltransferase (ChAT); 3) the storage of ACh in synaptic vesicles; 4) release of neurotransmitter into the synapse in response to a stimulus; and 5) degradation of ACh within the synaptic cleft, mediated by acetylcholinesterase (AChE), to regenerate choline. The latter is subsequently recycled. Given the multivariate nature of this system, regulation of cholinergic function may be accomplished in multiple ways. The synthesis of ACh takes place in the cytoplasm. However, ACh is subsequently stored in special organelles called synaptic vesicles. In response to a stimulus, these vesicles fuse with the presynaptic membrane and release their contents into the synapse. Neurotransmitter is characteristically released in discrete amounts or quanta. Therefore, the synaptic vesicle largely defines the unit of ACh release. The release of neurotransmitter is in turn inextricably linked to its storage. Consequently, interference with storage mechanisms provides a means of modulating the release of acetylcholine and thereby modulating cholinergic function.

The lipophilic amino alcohol 2-(4-phenylpiperidino)cyclohexanol (1, vesamicol, AH 5183) induces respiratory paralysis, spasms and death in laboratory animals (Brittain et al, 1969). The pharmacological activity of vesamicol is attributed to its ability to block cholinergic neurotransmission. The latter process is accomplished by the binding of vesamicol to a unique site, the vesamicol receptor, on the cholinergic synaptic vesicle. The vesamicol receptor is functionally linked to the vesicular ACh transporter (Marien et al., 1991), a protein complex which transports ACh from the cytoplasm into the vesicle. Occupancy of the vesamicol receptor by vesamicol or its analogs blocks the storage and subsequent release of ACh, thereby effectively shutting down cholinergic neurotransmission (for review, see Marshall & Parsons, 1987; Parsons et at., 1993). Vesamicol selectively inhibits the storage and release of neurotransmitter without directly affecting the synthesis of this neurotransmitter. The foregoing observations suggest that selective blockade of the vesamicol receptor may provide a means of modulating cholinergic function in animals.

In spite of its potency as an anticholinergic, vesamicol exhibits α-adrenoceptor activity at higher doses. The poor selectivity of this compound limits its use as a selective anticholinergic. Although Rogers et al. (1989) expressed a need for more potent and selective analogs, they failed to suggest methods for increasing potency. Previous studies by Rogers et al. (1989) have shown that 2-aminoethanol fragment of vesamicol is essential for molecular recognition at the vesamicol receptor. In addition, these authors showed that potent VR ligands could be obtained by substitution at the C4-carbon of vesamicol and by ring fusion on the cyclohexyl fragment of vesamicol. In a subsequent study, Efange et al. (1991) reported the synthesis of acyclic vesamicol analogs represented by HBrPP (2a)(FIG. 1). Although 2a lacks the cyclohexyl moiety found in vesamicol, the former was nevertheless found to be equipotent with vesamicol. The latter observation was attributed to the ability of this acyclic analog to adopt a conformation similar to that found in the fused analog ABV (2b), a potent VR ligand. Further exploration of the structure-activity relationships of vesamicol receptor ligands has yielded trozamicol, 3, (Efange et al., 1993), the parent structure for a new class of vesamicol receptor ligands. Although trozamicol is a poor ligand for vesamicol receptor, N-benzylation of trozamicol yields potent ligands such as MIBT, 4, (Efange et al., 1993). In the present study we disclose a new approach to the development of potent vesamicol receptor ligands for modulating presynaptic cholinergic function.

The vesamicol structure may be divided into three major fragments: the cyclohexyl (fragment A), piperidyl (fragment B), and phenyl (fragment C) moieties. In their original investigation, Rogers et al. (1989) carried out extensive modification of all three fragments with varying results. In general, single-point modifications in fragment B or C were found to yield analogs of slightly lower or comparable potency relative to vesamicol. On the other hand, those analogs which represented drastic structural alterations of the piperidyl and phenyl moieties (fragments B and C) were found to be inactive. For example, chlorovesamicol (1b) and nitrovesamicol (1c) and the piperazine-containing analogs 5a–c were between two and eight times less potent than vesamicol. However, the tetrahydroisoquinoline analog 6a was found to be 125 times less active than vesamicol. In addition, the spirofused compound 6b and other analogs (e.g., 7a and 7b) which incorporate fragments B and C in a complex molecule were also found to be inactive. These results clearly suggested that drastic structural modification of fragments B and C would not be fruitful.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

In our search for more potent and selective vesamicol analogs, we postulated that a complex amine-containing molecule can successfully replace fragments B and C as long as the following conditions are fulfilled: a) the elements of fragments B and C are contained within this complex molecule; and b) fragment B is constrained in an orthogonal or near-orthogonal orientation relative to fragment C. The simplest structures which fulfill both requirements are spirofused piperidines. Representative compounds from three classes of these spirofused piperidines, spiro[indene-1(1H), 4'-piperidine](compound 8), 2,3-dihydrospiro[indene-1,4'-piperidine](compound 9) and spiro[naphthalene-1(2H),4'-piperidine] (compound 10) (FIG. 2), were designed, synthesized and tested in vitro for binding to the vesamicol receptor. Representative compounds from this group were then tested for anticholinergic activity in rats and mice. Henceforth, we will refer to this class of vesamicol receptor ligands as SPIROVESAMICOLS.

These spirovesamicols have relatively poor affinity to human sigma receptors while binding well to vesamicol receptors. This makes the spirovesamicol excellent cholinergic probes. These compounds may be radiolabeled and used as reliable targets for radiotracer development. They may be used as agents to detect Alzheimer's Disease. Additionally, since the compounds of the invention are anticholinergics, they may be used where anticholinergics are desired, such as in pesticides or muscle relaxants. The radiolabel may be a transition metal or any acceptable tag which will make the compound detectable outside the brain. Finally, these new agents may be used for therapeutic applications which require a down regulation of cholinergic function.

BRIEF DESCRIPTION OF THE DRAWINGS

A detailed description of the invention is hereafter described with specific reference being made to the drawings in which:

FIGS. 11–16 shows Scheme 1, the synthesis of spirovesamicols;

FIG. 5 shows the potency of vesamicol analogs at human sigma receptors.

DESCRIPTION OF THE PREFERRED EMBODIMENTS

Chemistry

Figure 1:
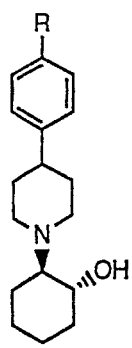
FIGS. 1–10 shows vesamicol and vesamicol analogs.
Figure 2:
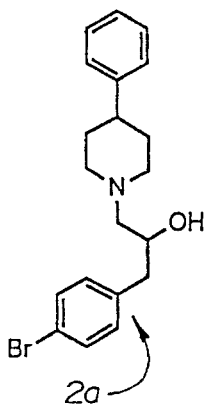
Figure 3:
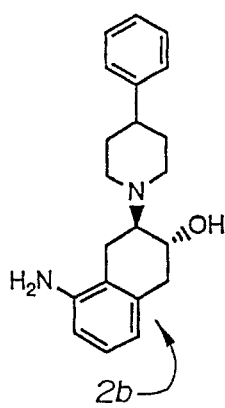
Figure 4:
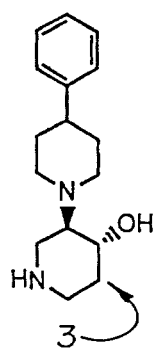

The target compounds were synthesized in moderate yields as described in the Experimental section (Schemes 1 and 2). The assignment of structure for compounds 20a–c is based on previous work on nonsymmetrical bipiperidyls (Efange et al., 1993).

Pharmacological Studies in Mice

In vivo anticholinergic activity was evaluated in Swiss Webster mice. Blockade of cholinergic neurotransmission (or anticholinergic activity) was manifested in a rapidly developing respiratory distress, spasms and paralysis. At lethal doses these symptoms were followed by death within 10–20 min. As evident in Tables 1 and 2, the representative compounds tested were lethal at doses as low as 10 umol/Kg. These data clearly demonstrate that these compounds exhibit anticholinergic activity in vivo.

Vesamicol Receptor Binding

Vesamicol receptor binding was performed according to methods published earlier (Kaufman et al., 1988) with the following modifications: higher concentrations of [$^3$H]vesamicol (approx. 5 nM) were used to compensate for the lower receptor concentration employed; 2) the assay mixtures were equilibrated for 24 h. Under the conditions of this assay, the dissociation constant ($k_d$) for (−)-vesamicol was determined to be 1.0 nM.

The relative potency of spirovesamicols is given on Table 3. In contrast to earlier observations by Rogers et at., we note that replacement of the phenylpiperidyl moiety of vesamicol with spiro[1H-indene-1,4'piperidine] yields several potent compounds. In fact all analogs tested, 11a–d and 11f, are 2 to 10 times more potent than vesamicol. Since the values given here are for the racemates, it is expected that the active enantiomers would be at least twice as active as these racemates. Therefore many of these compounds may be up to twenty times more potent than vesamicol. The incorporation of a bromine atom into the indene structure was generally found to increase or maintain potency. However, the presence of bromine at the C6 position (compound 17) was unfavorable as indicated by the slight reduction in potency (11a vs 17). In contrast, substitution at C2 resulted in 20-fold increase in potency (11a vs 14), suggesting significant bulk tolerance at this position.

Of the four analogs of compound 10 tested, three are less potent than vesamicol. While this observation would appear to suggest that the spiro[naphthalene-1,4'-piperidine] moiety is unsuitable, one analog, 13d, is at least ten times more potent than (−)-vesamicol. In fact 13d is one of the most active spirovesamicols. These results suggest that spirofused nitrogen-containing heterocycles may be used to replace the 4-phenylpiperidyl fragment of vesamicol to develop potent vesamicol ligands for modulating cholinergic transmission.

Experimental

General Section

Synthetic intermediates were purchased from Aldrich, Inc. (Milwaukee, Wis.) and were used as received. Solvents were distilled immediately prior to use. Commercially available reagents were used without subsequent purification.

All air-sensitive reactions were carried out under nitrogen. Standard handling techniques for air-sensitive materials were employed throughout this study. Melting points were determined on a Mel-Temp melting point apparatus and are uncorrected. The specific rotation was determined on an automatic polarimeter (Autopol III, Rudolph Research, Flanders, N.J.). $^1$H NMR spectra were recorded on an IBM-Brucker spectrometer at 200 MHz. NMR spectra are referenced to the deuterium lock frequency of the spectrometer. Under these conditions, the chemical shifts (in ppm) of residual solvent in the $^1$H NMR spectra were found to be as follows: CHCl$_3$, 7.26; DMSO, 2.56; HOD, 4.81. The following abbreviations are used to describe peak patterns when appropriate: br=broad, s=singlet, d=doublet, t=triplet, q=quartet, m=multiplet. Both low- and high-resolution MS were performed on an AEI MS-30 instrument. Elemental analyses were performed by Atlantic Microlab, Inc., Norcross, Ga., and are provided in Table 4. Unless otherwise indicated, these values are within ±0.4% of the theoretical.

Column chromatography was performed using "Baker Analyzed" silica gel (60–200 mesh). Preparative chromatography was performed on either a Harrison Research Chromatotron using Merck 60 PF$_{254}$ silica gel or a preparative HPLC (Rainin Instrument Co.) using a 41.1 mm ID Dynamax silica gel column (at a solvent delivery rate of 80 ml/min.). Enantiomeric purity was determined by HPLC with a Chiralcel OD column (isopropyl alcohol: hexane: Et$_3$N, 10:89:1; flow rate 1 ml/min.). Analytical TLC was performed on Analtech glass TLC plates coated with silica gel GHLF and were visualized with UV light and/or methanolic iodine. All target compounds were checked for purity by HPLC (silica gel, 10–20% isopropyl alcohol-hexanes, trace Et$_3$N).

Procedure A

1'-(2-Hydroxycylohex-1-yl)spiro[1H-indene-1,4'-piperidine]Hydrochloride (11a)

Spiro[1H-indene-1,4'-piperidine]hydrochloride was prepared by the method described earlier by Evans et al. (1992).

A mixture of commercially available cyclohexene oxide (0.22 g, 2.24 mmol) and spiro[1H-indene-1,4'-piperidine] hydrochloride in EtOH (20 mL) and triethylamine (5 mL) was refluxed for 21 h, cooled to room temperature and concentrated in vacuo. The residue was dissolved in a min volume of $CH_2Cl_2$ and the solution was applied onto a short column of silica gel which was subsequently eluted with acetone(20):hexanes(79):Et$_3$N(1). The eluent was concentrated in vacuo to yield a dark red syrup (0.35 g, 55%) which was judged by tlc to be greater than 95% pure. The syrup was dissolved in MeOH, and cooled in an icebath. Dry HCl gas was then bubbled through this solution, thereby converting the free base to the corresponding hydrochloride. The solvent was removed in vacuo to yield a solid which was recrystallized from isopropyl alcohol to provide a light tan solid; mp 280°–283° C.; $^1$H NMR (CDCl$_3$) δ1.20–2.29 (m, 12, piperidyl+eychohexyl), 2,74 (d,2, piperidyl α-H, J=5.6 Hz), 2.95 (d,2,piperidyl) 3.45 (m, 1, cyclohexyl CH$_2$CHNCHOH), 3.70 (m, 1, cyclohexyl CH$_2$CHNCHOH), 6.72 (d, 1, indenyl C2-H, J=5.7 Hz), 6.82 (1, d, indenyl C3-H, J=5.7 Hz), 7.16–7.39 (m, 5, aryl). Anal. ($C_{19}H_{25}NO·HCl$) C,H,N.

Procedure B

1'-(2-Hydroxy-1,2,3,4-tetrahydronaphth-3-yl)-spiro[1H-indene-1,4'-piperidine]Hydrochloride (11b)

A biphasic mixture of the bromohydrin (1.14 g, 5.0 mmol) in 2M aq. NaOH (100mL) and CHCl$_3$ (100 mL) was refluxed for 2.5 h. TLC (silica gel; 50% hexane-CH$_2$Cl$_2$) confirmed that formation of the epoxide was complete. The mixture was cooled to room temperature and the two layers were separated. The aq. phase was re-extracted with CHCl$_3$ (2×30 mL) and discarded. The organic extracts were combined, dried over anhydrous Na$_2$SO$_4$ and concentrated under reduced pressure to yield the crude epoxide as a pale yellow syrup which was redissolved in EtOH (30 mL) and Et$_3$N (2 mL). Spiro[1H-indene-1,4'-piperidine]hydrochloride (1.11 g, 5.0 mmol) was added to this solution, and the resulting mixture was refluxed overnight. After 17 h, heating was stopped. The mixture was cooled to room temperature and concentrated to a residue in vacuo. The residue was dissolved in CH$_2$Cl$_2$ (50 mL) and the solution was washed with satd aq. NaHCO$_3$ (30 mL). The aqueous extract was washed with CH$_2$Cl$_2$ (30 mL) and discarded. The organic extracts were combined, dried over anhydrous Na$_2$SO$_4$ and concentrated to a residue. The latter was dissolved in a minimum volume of CH$_2$Cl$_2$ and applied to a short column of silica gel which was subsequently eluted with 25% acetone-hexane. Concentration of the eluent yielded the product (0.91 g, 55%) as a brown syrup. The latter was estimated by tlc (silica gel, acetone(25):hexane (74):Et$_3$N (1)) to be greater than 97% pure. The corresponding hydrochloride was prepared in MeOH as outlined for (11a) above, and recrystallized from isopropyl alcohol; mp 254°–257° C.; $^1$H NMR (CDCl$_3$) δ1.46 (d, 2, piperidyl β-H$_{eq., J}$=12.8 Hz), 2.17 (m, 2, piperidyl β-H$_{ax}$), 2.86–3.49 (m, 8, tetrahydronaphthyl C1-H, C3-H, C4-H & piperidyl α-H$_{ax.,eq.}$), 3.93–4.20 (m, 3, piperidyl α-H$_{eq}$ & CHOH), 6.79 (d, 1, indenyl C2-H, J=5.6 Hz), 6.90 (d, 1, indenyl C3-H, J=5.7 Hz), 7.03–7.42 (m, 8, aryl).

Procedure C

Preparation of
1'-(1-butoxycarbonyl,3-Hydroxypiperidin-4-yl)-spiro[1H-indene-1,4'-piperidine](19a) and
1'-(1-butoxycarbonyl-4-Hydroxypiperidin-3-yl)-spiro[1H-indene-1,4'-piperidine](20a)

A solution of 1,2,3,6-tetrahydropyridine in CH$_2$Cl$_2$ (10 mL) was added to a stirring solution of di-tert-butyldicarbonate in CH$_2$Cl$_2$ (40 mL). The resulting mixture was treated with Et$_3$N (1 mL) and stirred overnight. After 30 h, the reaction mixture was concentrated to provide a clear colorless liquid which was redissolved in THF (100 mL). To this solution was added N-bromosuccinimide (4.45 g, 25.0 mmol) and water (25 mL). The resulting biphasic mixture was stirred at room temperature for 23 h, diluted with water (40 mL) and extracted with CH$_2$Cl$_2$ (2×50 mL). The combined organic extracts were dried over anhyd Na$_2$SO$_4$ and concentrated under reduced pressure to a syrup. The latter was triturated with hot hexane and cooled to cause precipitation of succinimide. The precipitate was removed by filtration and discarded. The filtrate was concentrated to provide a mixture of the isomeric bromohydrins as a yellow syrup (6.8 g, 98%). A fraction of this syrup (3.64 g, 13.0 mmol) was refluxed for 2 h in a biphasic mixture of CHCl$_3$ (100 mL) and 2.5M aq. NaOH (100 mL). The mixture was allowed to cool to room temperature and the layers were separated. The aq. layer was re-extracted with CHCl$_3$ (2×30 mL) and discarded. The combined organic extracts were dried over anhyd Na$_2$SO$_4$ and concentrated to yield N-tert-butoxycarbonyl-1,2,3,6-tetrahydropyridine oxide (2.72 g) as an orange liquid. A mixture of the crude epoxide (2.72 g) and 8 (2.22 g, 10.0 mmol) in EtOH (60 mL) and Et$_3$N (15 mL) was refluxed for 24 h, cooled and concentrated to a residue. The latter was partitioned between CH$_2$Cl$_2$ (50 mL) and water (40 mL). Following separation of the layers, the aq. phase was re-extracted with CH$_2$Cl$_2$ (50 mL). The organic extracts were combined, dried over anhyd. Na$_2$SO$_4$, conc to a minimum volume and passed through a short column of silica gel (eluting with 20% acetone(20):hexane(79):Et$_3$N(1)). Concentration of the eluent provided a red syrup which was subjected to preparative HPLC (5:94:1 i-PrOH/hexane/Et$_3$N; flow rate, 80 mL/min). Concentration of the more mobile fraction yielded 19a (0.61 g, 16%) as a syrup. () $^1$H NMR (CDCl$_3$) δ1.45 (broad s, 9, (CH$_3$)—C), 1.70–1.90 (m, 2, piperidyl), 2.01 (td, 1, piperidyl), 2.11–2.28 (m, 2, piperidyl), 2.38–2.70 (m, 2, piperidyl), 2.76–3.00 (m, 3, piperidyl), 3.47 (m, 1, piperidyl), 3.67 (m, 1, piperidyl), 3.91–3.40 (m, 2, piperidyl), 4.15 (m, 1, N—CH—CHOH), 4.28 (broad s, 1, HC—OH), 4.45 (broad S, 1,—OH) 6.74 (d, 1, J=6 Hz, ph-CH=CH), 6.80 (d, 1, J=6 Hz, ph-CH=CH—), 7.20–7.39 (m, 4, phenyl). The less mobile fraction, 20a (1.90 g, 49%) was obtained as the major component. $^1$H NMR (CDCl$_3$) δ1.52 (m, 11, (CH$_3$)$_3$—C, piperidyl), 1.99–2.35 (m, 4, piperidyl), 2.40 (td, 1, piperidyl), 2.61 (td, 1, piperidyl), 2.72–2.82 (m, 3, piperidyl), 2.92 (m, 1, piperidyl), 3.07 (m, 2, piperidyl), 3.63 (m, 1, N—CH—CHOH), 4.13 (broad s, 1, HC—OH), 4.38 (broad s, 1, —OH), 6.74–6.80 (complex dd, 2H, indyl), 7.18–7.41 (m, 4, phenyl). Anal. ($C_{23}H_{32}N_2O_3$) C,H,N.

Resolution of 20a

Racemic 20a was resolved on a Chiralcel OD column (20% i-PrOH-hexane) to yield 0.8 g of (+)-20a and 0.8 g of (−)-20a (64% recovery).

(+)-20a:retention time, 14.6 min;[α]$_D$=+38.72° (C=0.02M, MeOH)

(−)-20a:retention time, 20.3 min;[α]$_D$=−38.95° (C=0.02M, MeOH)

(+)-1'-(4-Hydroxypiperidin-3-yl)spiro[1H-indene-1,4'-piperidine]dihydrochloride {(+)-21a} and (−)-1'-(4-Hydroxypiperidin-3-yl)spiro[1H-indene-1,4'-piperidine]dihydrochloride {(−)-21a}

Solutions of (+)-20a and (−)-20a in EtOAc (20 mL) were cooled down to 0° C. Dry HCl gas was bubbled through these solutions for 30 min with stirring. The stirring was continued for additional 30 min at 0° C. The solutions were concentrated under reduced pressure to yield (+)-21a (0.62 g, 84%) and (−)-21a (0.69 g, 93%), respectively; mp 279°–282 °C.

Procedure D

1'-(4-Hydroxy1-(2-iodobenzyl)piperidin-3-yl)-spiro[1H-indene-1,4'-piperidine]dihydrochloride (11c)

A mixture of sodium bicarbonate (0.42 g, 5.0 mmol), 2-iodobenzyl chloride (0.23 g, 0.92 mmol) and 1'-(4-hydroxypiperidin-3-yl)spiro[1H-indene-1,4'-piperidine]dihydrochloride (0.30 g, 0.84 mmol) in EtOH (13 mL) and water (6 mL) was refluxed for 23 h. The resulting mixture was cooled and concentrated under reduced pressure. The residue was partitioned between $CH_2Cl_2$ (30 mL) and water (25 mL). After separation of the layers, the aq. layer was re-extracted with $CH_2Cl_2$ (2×30 mL) and discarded. The combined organic layers were dried over anhyd $Na_2SO_4$ and concentrated to a residue which was purified by radial flow chromatography on silica gel (13:86:1 acetone/hexane/triethylamine) to yield 0.13 g (31%) of the free base as a pale yellow syrup. The latter was converted to the corresponding hydrochloride in methanol as described above, and recrystallized from i-PrOH to give a white solid; mp 242°–245° C. The yield was increased to 71% when Procedure E was used. $^1H$ NMR ($CDCl_3$) δ1.36 (d, 2, piperidyl), 1.66 (dt, 1, piperidyl), 2.04–2.27 (m, 5, piperidyl), 2.57 (t, 1, piperidyl), 2.64 (dt, 1, piperidyl), 2.70–3.52 (m, 5, piperidyl), 3.57–3.62 (m, 3, benzyl,piperidyl), 3.80 (broad s, 1, OH—), 6.73 (d, J=6 Hz, 1, Ph—CH=C$\underline{H}$), 6.80 (d, J=6 Hz, 1, Ph—C$\underline{H}$=CH), 6.96 (t, J=9 Hz, 1, iodophenyl), 7.21–7.44 (m, 6H, iodophenyl, phenyl), 7.84 (d, 1, J=6 Hz, iodophenyl).

Procedure E

1'-(4-Hydroxy1-(3-iodobenzyl)piperidin-3-yl)-spiro[1H-indene-1,4'-piperidine]dihydrochloride (11d)

A mixture of 21b (0.30 g, 0.84 mmol), 3-iodobenzyl bromide (0.25 g, 0.84 mmol) and $K_2CO_3$ (0.4 g, 2.89 mmol) was stirred in DMF (20 mL) at room temperature for 18 h. The reaction mixture was diluted with $CH_2Cl_2$ (50 mL) and filtered, diluted with $H_2O$ (100 mL), the organic layer was separated and the aqueous layer was re-extracted with $CH_2Cl_2$ (50 mL). The combined organic extracts were dried over $Na_2SO_4$, concentrated under reduced pressure to obtain a liquid residue. The residue which was purified by passing through a short silica gel column (33% acetone-hexane). The eluent was concentrated under reduced pressure to obtain a yellow syrup (0.29 g, 71%). The free base was converted to the dihydrochloride using methanolic HCl; m.p. 226°–228° C. $^1H$ NMR ($CDCl_3$) δ1.35 (d, 2, piperidyl), 1.64 (dt, 1, piperidyl), 1.93–2.25 (m, 5, piperidyl), 2.54 (t, 1, piperidyl), 2.66(dt, 1, piperidyl), 2.79–3.10 (m, 5, piperidyl), 3.40–3.56 (m, 3, benzyl,piperidyl), 3.80 (broad s, 1, OH—), 6.72 (d, J=6 Hz, 1, Ph—CH=C$\underline{H}$), 6.80 (d, J=6 Hz, 1, Ph—C$\underline{H}$=CH), 7.06 (t, J=9 Hz, 1, iodophenyl), 7.20–7.36 (m, 5, iodophenyl, phenyl), 7.58 (d, 1, iodophenyl), 7.69 (s, 1, iodophenyl).

1'-(4-Hydroxy1-(4-iodobenzyl)piperidin-3-yl)-spiro[1H-indene-1,4'-piperidine]dihydrochloride (11e)

Procedure E

Yield, 52%; mp (ether-isopropyl alcohol) 243°–245° C. $^1H$ NMR ($CDCl_3$) δ1.35 (d, 2, piperidyl), 1.62 (dt, 1, piperidyl), 1.92–2.30 (m, 5, piperidyl), 2.56 1 (m, 2, piperidyl), 2.86–3.07 (m, 5, piperidyl), 3.40–3.57 (m, 3, benzyl, piperidyl), 3.81 (broad S, 1,—OH), 6.72 (d, 1, J=6 Hz, Ph—CH=CH—), 6.79 (d, 1, J=6 Hz, Ph—CH=CH—), 7.07 (d, 2, J=8Hz, Iodophenyl), 7.17–7.36 (m, 4, phenyl), 7.64 (d, 2, J=8 Hz, iodophenyl).

1'(4-Hydroxy-1-(2-fluorobenzyl)piperidin-3-yl)-spiro[1H-indene-1,4'-piperidine]dihydrochloride (11f)

Procedure E

Yield, 66%; m.p.(acetone) 126°–128° C. $^1H$ NMR (($CDCl_3$) δ1.36 (d, 2, piperidyl), 1.64 (dt, 1, piperidyl), 1.94–2.16(m, 6, piperidyl), 2.62 (t, 1, piperidyl), 2,79–3.13 (m, 5, piperidyl), 3.40–3.56 (m, 3, benzyl piperidyl), 3.80 9 broad s, 1, OH—), 6.75 (d, J=6 Hz, 1, Ph—CH=C$\underline{H}$), 6.78 (d, J=6 Hz, 1, Ph—C$\underline{H}$=CH), 7.01 (t, J=8 Hz, 2, fluorophenyl), 7.18–7.36 (m, 6, fluorophenyl, phenyl).

1'-Benzyl-2,3-Dihydrospiro[indene-1,4'-piperidine](31)

4-(2-Phenylethyl)pyridine (8.5 g, 46 mmol) and benzyl chloride (11.64 g, 92 mmol) were refluxed in acetone for 48 h. The precipitated 1-benzyl-4-(2-phenylethyl)pyridinium chloride was filtered, washed with acetone and dried in vacuo at 50° C. to obtain 9.35 g (65%) off the white solid. 1-Benzyl-4-(2-phenylethyl)pyridinium chloride (9.0 g, 29.0 mmol) was suspended in MeOH (100 mL) and cooled to 0° C. in an ice bath. $NaBH_4$ (4.73 g, 207.2 mmol) was added portionwise with vigorous stirring over 40 min. After cooling and stirring for an additional 1 h, the reaction mixture was concentrated under reduced pressure and partitioned between $H_2O$ (50 mL) and $CH_2Cl_2$ (50 mL). The layers were separated, and the aqueous phase was re-extracted with $CH_2Cl_2$ (50 mL). The combined $CH_2Cl_2$ extracts were dried over $Na_2SO_4$, and concentrated under reduced pressure to provide 7.1 g (91%) of 1-benzyl-4-(2-phenylethyl)-1,2,3,6-tetrahydropyridine as a pale yellow oil. $^1H$ NMR (($CDCl_3$) δ2.14 (br s, 2, N—$CH_2$—$CH_2$—CH=), 2.27 (t, 2, J=8 Hz, N—C$\underline{H}_2$—$CH_2$—), 2.57 (t,2, J=6 Hz, Ph—C$\underline{H}_2$—$CH_2$—), 2.73 (m, 2, Ph—$CH_2$—C$\underline{H}_2$—), 2.97 (br s, 2, N—C$\underline{H}_2$—CH=), 3.59 (s, 2, Ph-$CH_2$—N), 5.41 (m, 1, CH=C—), 7.14–7.38 (m, 10, phenyl). 1-Benzyl-4-(2-phenylethyl)-1,2,3,6-tetrahydropyridine (7.1 g, 25.6 mmol) was refluxed in 85% $H_3PO_4$ (50 mL) for 80 h. The reaction mixture was basified with 6N $NH_4OH$ and extracted with ether (2×100 mL). The ethereal extracts were dried over $MgSO_4$ and concentrated under reduced pressure to a residue. The crude product was purified by radial flow chromatography on silica (hexane,9:acetone,1) to yield 2.3 g (32%) of 1'-benzyl-2,3-dihydrospiro[indene-1,4'-piperidine] as a straw colored liquid. $^1H$ NMR ($CDCl_3$) δ1.53 (br d, 2, piperidyl β-$H_{eq}$.), 1.96 (dt, 2, piperidyl β-$H_{ax}$),2.02 (t, 2, Ph—$CH_2$—C$\underline{H}_2$—, J=6 Hz, ), 2.20 (dt, 2, piperidyl α-$H_{ax}$), 2.90 (m, 4, Ph-C$\underline{H}_2$—$CH_2$— & piperidyl α-$H_{eq}$), 3.59 (s, 2, benzyl), 7.14–7.40 (m, 9, phenyl).

2,3-Dihydrospiro[1H-indene-1,4'-piperidine]Hydrochloride (9)

1'-Benzyl-2,3-dihydrospiro[1H-indene-1,4'-piperidine] (0.50 g, 1.80 mmol) was dissolved in dichloroethane (6 mL). The resulting solution was cooled to 0° C. and 1-chloroethylchloroformate (0.258 g, 1.80 mmol) was added in one batch. Cooling was continued for 10 min after which the reaction mixture was refluxed for 1 h, cooled to room temperature and concentrated under reduced pressure. The residue was redissolved in MeOH (10 mL) and refluxed for 2 h. The resulting solution was concentrated under reduced pressure to obtain (0.40 g, quant.) of a pale yellow crystalline solid; m.p. 256°–257° C. (lit. 288–290); $^1$H NMR (CDCl$_3$): δ1.74 (br d, 2, piperidyl β-NH$_{eq}$), 2.10 (td, 2, piperidyl β-H$_{ax}$), 2.13 (t, 2, Ph—CH—CH$_2$—CH$_2$—, J=6 Hz), 2.94 (t, 2, J=6 Hz, Ph—CH$_2$—CH$_2$—), 3.12–3.38 (m, 4, piperidyl α-H$_{ax,eq}$), d=7.19 (br s, 4, phenyl). MS (EI) m/e 187.2 (M$^+$ of free base).

2,3-Dihydro-1'-(2-Hydroxycylohex-1-yl)spiro[1H-indene-1,4'-piperidine]Hydrochloride (12a)

Procedure A

Yield, 60%; m.p. 264°–267° C. $^1$H NMR (CDCl$_3$) δ1.25 (broad d, 2, eqi.piperidyl(N—CH$_2$—CH$_2$–)), 1.76–2.94 (m, 15, cyclohexyl, piperidyl), 2.00 (t, 2, J=6 Hz, Ph—CH$_2$—CH$_2$—), 2.77 (t, 2, J=6 Hz, Ph—CH$_2$—CH$_2$—), 3.40 (m, 1, C H—OH), 4.17 (broad s, 1, —OH), 7.25 (s, 4, phenyl).

1'-(2-Hydroxy- 1,2,3,4-tetrahydronaphth-3-yl)-2,3-dihydrospiro[1H-indene-1,4'-piperidine]hydrochloride (12b)

Procedure B

Yield, 48%; mp 267°–269° C. $^1$H NMR (CDCl$_3$) δ1.86 (br d, 2, piperidyl β-Heq.), 2.04 (td, 2, piperidyl β-Hax), 2.08 (t, 2, J=6 Hz, Ph—CH$_2$—CH$_2$—), 2.45 (td, 1, piperidyl α-Hax), 2.84 (m, 9, piperidyl αHeq, cyclohexyl, Ph—C H$_2$—CH$_2$—), 3.33 (dd, 1, eqi. piperidyl(N—C H$_2$—CH$_2$—)), 3.92 (m, 1, CH—OH), 4.47 (broad s, 1, OH—), 7.15 (s, 4, phenyl(spiro)), 7.32 (m, 5, phenyl).

1'-(1-t-butoxycarbonyl-3-hydroxypiperidin-4-yl)-2,3-dihydrospiro[indene-1,4'-piperidine] (19b) and
1'-(1-t-butoxycarbonyl-4-hydroxypiperidin-3-yl)-2,3-dihydrospiro[indene-1,4'-piperidine] (20b)

Procedure C. 19b

Yield, 14%. $^1$H NMR (CDCl$_3$) δ1.45 (s, 9H,t-butyl), 1.56 (m, 2, piperidyl), 1.86 (m, 4, piperidyl), 1.97 (t, J=6 Hz, 2, Ph—CH$_2$—CH$_2$—), 2.32 (m, 2, piperidyl), 2.55 (m, 3, piperidyl), 2.88 (t, J=6 Hz, 2, Ph—CH$_2$—CH$_2$—), 3.85 (m, 1, piperidyl), 3.95 (m, 1, piperidyl), 4.22 (br d, 1, piperidyl), 4.40 (br d, 1, piperidyl), 7.17 (s, 4, phenyl).
20b Yield, 25%; $^1$H NMR (CDCl$_3$) δ1.45 (s, 9H, t-butyl), 1.56 (m, 2, piperidyl), 1.74–2.11 (m, 7, Ph—CH$_2$—CH$_2$ —piperidyl), 2.38 (m, 2, piperidyl), 260 (m, 4, piperidyl), 2.89 (t, J=6 Hz, 2, Ph—CH$_2$—CH$_2$—),3.58 ( m, 1, piperidyl), 3.68 (m, 1, piperidyl), 4.13 (m, 1, piperidyl), 4.27 (broad d, 1, piperidyl), 7.18 (s, 4, phenyl).
Resolution of 20b Racemic 20b (0.6 g, 1.55 mmol) was resolved on Chiralcel OD column (30:70 i-PrOH:hexane (trace Et$_3$N)) to yield 0.22 g of (+)-20b and 0.23 g of (–)-20b. (75% recovery). (+)-20b: retention time, 12.5 min;[α]=+28.74° (c=0.02M, MeOH) (–)-20b: retention time, 18.2 min;[α]=+28.87° (c=0.02M,MeOH).

(+)-1'-(4-Hydroxypiperidin-3-yl)-2,3-dihydrospiro[indene-1,4'-indene]hydrochloride
{(+)-21b } and
(+)-1'-(4-Hydroxypiperidin-3-yl)-2,3-dihydrospiro[indene-1,4'-piperidene]hydrochloride
{(–)-21b}

Solutions of (+)- and (–)-20b in EtOAc (20 mL) were cooled down to 0° C. Dry HCl gas was bubbled through these solutions for 30 min. with stirring. The stirring was further continued for additional 30 min. at 0° C. The solutions were concentrated under reduced pressure to yield the corresponding deprotected hydrochlorides, (+)-21b (92%) and (–)-21b (90%); m.p. 280°–283° C.

(dl)-1'-(4-Hydroxypiperidin-3-yl)-2,3-dihydrospiro[indene-1,4-piperidine]dihydrochloride (21b)

Method 2: A mixture of 21a (1.2 g, 3.35 mmol) and 10% Pd-C (0.2 g) in MeOH (50 mL) was hydrogenated for 3 h at 50 psi. The catalyst was filtered and the filtrate was concentrated under reduced pressure to yield an off-white solid (1.12 g, 93%). m.p. 280°–283° C.

$^1$H NMR δ=1.79 (d, 2, piperidyl), 1.96 (dt, 1, piperidyl), 2.14 (t, J=8 Hz, 2, Ph—CH$_2$—CH$_2$—), 2.35 (m, 4, piperidyl), 2.95 (t, J=8 Hz, 2, Ph—CH$_2$—CH$_2$—), 3.10–374 (m, 9, piperidyl), 4.05 (d, 1, piperidyl), 4.28 (dt, 1, piperidyl), 7.11–7.39 (m, 4, phenyl).

1'-(4-Hydroxy1-(2-iodobenzyl)piperidin-3-yl-2,3-dihydrospiro[indene-1,4'-piperidine]dihydrochloride (12c)

Procedure E

Yield, 39%; m.p.(i-PrOH-ether) 246°–249° C.
$^1$H NMR (CDCl$_3$) δ1.59 (m, 2, piperidyl), 1.80–2.10 (m, 8, piperidyl,indane), 2.31 (t, 1, piperidyl), 2.51 (t, 1, piperidyl), 2.67–3.10 (m, 7, piperidyl,indane), 3.40–3.54 (m, 3, benzyl, piperidyl), 4.05 (broad s, 1, —OH), 6.95 (t, 1, iodophenyl), 7.16–7.30 (m, 5, iodophenyl, phenyl), 7.32 (d, 1, iodophenyl), 7.81 (s, 1, iodophenyl).

1'-(4-Hydroxy-1-(3-iodobenzyl)piperidin-3-yl)-2,3-dihydrospiro[indene-1,4'-piperidine]dihydrochloride (12d)

Procedure E

Yield, 73%; m.p. (i-PrOH-ether) 243–246° C.
$^1$H NMR (CDCl$_3$) δ1.50 (m, 2, piperidyl), 1.78 (dt, 1, piperidyl), 1.88–2.02 (m, 7, piperidyl,indane), 2.31 (t, 1, piperidyl), 2.54(t, 1, piperidyl), 2.67–3.00(m, 7, piperidyl, indane), 3.40–3.51 (m, 3, benzyl,piperidyl), 3.80 (broad s, 1, —OH), 7.03 (t, J=9 Hz, 1, iodophenyl), 7.14–7.28 (m, 5, iodophenyl, phenyl), 7.57 (d, 1, iodophenyl), 7.66 (s, 1, iodophenyl).

1'-(4-Hydroxy1-(4-iodobenzyl)piperidin-3-yl)-2,3-dihydrospiro[indene-1,4'-piperidine]dihydrochloride (12e)

Procedure E

Yield, 50%: mp (i-PrOH-ether) 248°–249° C. $^1$H NMR (CDCl$_3$) δ1.51 (m, 2, piperidyl), 1.67–1.93 (m, 8, piperidyl, indane), 2.35 (t, 1, piperidyl), 2.57 (dt, 1, piperidyl), 2.75–3.04 (m, 7, piperidyl, indane), 3.41–3.54 (m, 3, benzyl, piperidyl), 3.80 (broad s, 1, —OH), 7.06 (d, 2, J=8 Hz, iodophenyl), 7.17–7.35 (m, 4, phenyl), 7.64 (d, J=8 Hz, iodophenyl).

1'-(4-Hydroxy1-(4-fluorobenzyl) piperidin-3-yl)-2,3-dihydrospiro[indene-1,4'-piperidine]oxalate (12f)

Procedure E

Yield, 84%; m.p. (i-PrOH-ether) 129°–131° C.

$^1$H NMR (CDCl$_3$) δ1.62 (m, 3, piperidyl), 1.78–2.06 (m, 7, piperidyl,indane), 2.37 (t, 1, piperidyl), 2.59 (dt, 1, piperidyl), 2.76–3.05 (m, 7, piperidyl,indane), 3.41–3.58 (m, 3, benzyl,piperidyl), 3.80 (broad s, 1, —OH), 7.01 (t, 2, fluorophenyl J=8 Hz), 7.14–728 (m, 6, fluorophenyl, phenyl).

Procedure F

3,4-Dihydro-1'-(2-Hydroxycyclohex-1-yl)-spiro[naphthalene-1,4'-piperidine]hydrochloride (13a)

A flask containing a mixture of 10 (505 mg, 2.51 mmol) in dichloromethane (2 mL) was maintained at 0° C. while Et$_3$Al (1.32 mL, 2.51 mmol)) was added dropwise. The solution was stirred at room temperature for 35 min. The flask was then placed in an ice bath and a solution of cyclohexene oxide (255 mL, 2.51 mmol.) in dichloromethane (75 mL) was added. The resulting mixture was stirred at room temperature for 18 h, while the disappearance of the epoxide was monitored by TLC (silica gel, ethyl acetate/hexanes, 50/50). When the reaction was complete (the solution became white), 5N KOH (2 mL) was added and stirring was prolonged for 2 h. Water (10 mL) was added and the mixture was extracted with dichloromethane (3×20 mL). After extraction, the combined organic extracts were washed with brine, dried (Na$_2$SO$_4$) and concentrated. The desired compound, 13a, was obtained as a white crystalline solid (598 mg, 80%); no impurities were observed by TLC (Silica gel, Ethyl acetate/hexanes: 50/50). The hydrochloride was prepared in methanolic HCl and the white solid was recrystallized from 50% ethyl acetate-hexanes; mp 306.6° C.; $^1$H-NMR (CDCl$_3$) δ2.24–1.22 (3 m, 16, piperidine+cyclohexanol), 2.46–2.52 (m, 2, Ph—CH$_2$), 2.65–2.79 (m, 4, Ph—CH$_2$—CH$_2$—CH$_2$), 2.98–3.02 (dt, 1, CHN), 3.42–3.47 (s, 1, CH—OH), 4.18 (s, 1, OH), 7.05–7.26 (m, 3, arom.), 7.45–7.49 (d, 1H, arom. J=7.7 Hz). Anal. (C$_{20}$H$_{29}$NO.HCl) C,H,N.

3,4-Dihydro-1'-(2-hydroxy-1,2,3,4-tetrahydronaphth-3-yl)-spiro[naphthalene-1(2H),4'-piperidine]hydrochloride (13c)

Crude 1,4-dihydronaphthalene (340 mg, 2.3 mmol), obtained from the corresponding bromohydrin as outlined for 11b above, was reacted with 10 following Procedure F to yield after purification on silica gel (ethyl acetate/hexanes/triethylamine, 50/50/1) a white solid (583 mg, 72%).The hydrochloride was prepared in methanolic HCl and recrystallized from ethyl acetate; mp 274.2° C. $^1$H NMR (CDCl$_3$) δ1.23–2.24 (m, 16, piperidine+cyclohexanol), 2.73–2.79 (m, 4, Ph—CH$_2$—CH$_2$—CH$_2$), 2.85–3.02(dt, 1, CHN), 3.30–3.45 (m, 1, CHOH), 4.18 (s, 1, OH), 7.05–7.26 (m, 7, arom.), 7.48–7.52 (d, 1, arom. J=7.6 Hz). Anal. (C$_{24}$H$_{29}$NO.HCl) C, H, N.

1'-(1-t-butoxycarbonyl-3-hydroxypiperidin-4-yl)-3,4-dihydro-spiro[naphthalene-1(2H),4'-piperidine](19c) and 1'-(1-t-butoxycarbonyl-4-hydroxypiperidin-3-yl)-3,4-dihydro-spiro[naphthalene-1(2H),4'-piperidine] (20c)

A mixture of the hydrochloride of 10 (4.9 g, 20.6 mmol) and 5.8g (21 mmol) of the isomeric bromohydrins derived from 1-t-butoxycarbonyl-1,2,3,6-tetrahydropyridine (see Procedure above) in absolute ethanol (25 mL) and triethylamine (15 mL) was refluxed for 24 h. Since TLC (silica gel, Hexanes/Ethyl acetate: 50/50) failed to show any progress in the reaction, solid potassium carbonate (7.26 g, 52.5 mmol) was added and the mixture was refluxed for four more days. After cooling, the salts were filtered off and the volatiles were removed under reduced pressure. The remaining brown oil was dissolved in ethyl acetate (30 mL) and the organic layer was successively washed with water (2×20 mL) and brine (20 mL), dried (Na$_2$SO$_4$) and concentrated. The mixture of 19c and 20c was obtained as an orange oil (6.7 g, 84%). The regioisomers were separated by preparative HPLC on a silica gel column(Hexanes/Isopropanol/Triethylamine: 98/2/0.02) to afford 1.58 g of 19c (retention time, 7 min) and 3.70 g of 20c (retention time, 8 min).

19c $^1$H NMR (CDCl$_3$) δ1.45 (s, 9, t-butoxy), 1.58–1.84 (m, 8, NCH$_2$—CH$_2$), 1.92–2.25(m, 2, Ar-CH$_2$—CH$_2$—CH$_2$), 2.35–2.54 (m, 6, CH$_2$—CH$_2$N(t-BOC—CH$_2$), 2.72–2.78 (m, 4, Ar—CH$_2$CH$_2$—CH$_2$) 2.87–2.98 (t, 1, CH—N, J=11.8 Hz), 3.38–3.50 (m, 1, CH—OH), 7.05–7.22 (m, 3, arom.), 7.43–7.46 (d, 1, arom. J=7.7 Hz).

20c $^1$H NMR (CDCl$_3$) δ1.47 (s, 9, 3 CH$_3$), 2.18–1.57 (2m, 8, 2N-CH$_2$—CH$_2$), 2.38–2.30 (dt, 2, CH$_2$—CHOH, J=3.6, 13.6), 2.57–2.49 (t, 2, Ar—CH$_2$, J=9.9), 2.64–2.58 (d, 2, N—CH$_2$—CHN, J=11.9), 2.78–2.75 (m, 4, Ar-CH$_2$—CH$_2$—CH$_2$), 3.09–2.98 (t, 2; CH$_2$—CH$_2$—N—tBOC, J=11.2), 3.66–3.54 (dt, 1, CH—N, J=4.6, 10.3), 3.83 (s, 1, CH—OH), 7.21–7.03 (m, 3, arom.), 7.45–7.42 (d, 1, arom. J=7.7 Hz).

Resolution of 20c

Separation of the two enantiomers (+)- and (−)-20c was performed on a 25 cm×10 mm id Chiralcel OD (Hexanes/Isopropanol/Triethylamine: 70/30/0.3)to afford (+)-20c (retention time: 10 min) and (−)-20c (retention time: 18 min) as white crystalline solids; (+)-20c: [α]$_D$=+30.2° (c=1.0, MeOH); (−)-20c: [α]$_D$=−30.9° (c=1.0, MeOH).

1'-(4-Hydroxypiperidin-3-yl)-3,4-dihydrospiro[naphthalene-1(2H),4'-piperidine]dihydrochloride (21c)

HCl gas was bubbled for 30 min through a soln of 20c (800 mg, 2.1 mmol) in EtOAc (10 mL) while the flask was maintained in an ice bath. The resulting solution was subsequently stirred at room temperature for 30 min, and the volatiles were removed under reduced pressure. The white solid thus obtained was recrystallized from 50% isopropyl alcohol-hexanes to provide the hydrochlorides of 21c as a white powder (80%).

Elemental analysis: Calc: C=61.12, H=8.1, N=7.5; Fnd: C=59.96, H=7.95, N=6.86.

1'-(1-(3-Iodobenzyl)-4-hydroxypiperidin-3-yl)-3,4-dihydrospiro[naphthalene-1(2H),4'- piperidine] (13d)

A mixture of 21c and 22c derived from a mixture of 19c and 20c as described above (676 mg, 1.81 mmol), 3-iodobenzylbromide (2.17 mmol, 645 mg), and triethylamine (10 mL) in absolute EtOH (20 mL) was refluxed for 18 h. Volatiles were removed under reduced pressure and the red residue was treated with water. After extraction in dichloromethane (3×30 mL), the combined organic layers were washed with brine, dried over Na$_2$SO$_4$ and concentrated to give a dark red semi-solid residue. Chromatographic purification (silica gel, 50% ethyl acetate-hexanes) afforded 276 mg (30%) of the crude product as a yellow oil. The two regioisomers were separated by HPLC (Silica gel, Hexane/ Isopropanol/Triethylamine: 98/2/0.02) and 13d was obtained as a white crystalline solid (166 mg, 18%). Only a trace of the other isomer was recovered. The hydrochloride of 13d was prepared in said methanolic saturated HCl and subsequently recrystallized from 50% i-PrOH-hexanes to provide a white powder; mp 245° C. $^1$H NMR ((CDCl$_3$) δ1.59–2.06 (m, 8, 2 N—CH$_2$—CH$_2$), 2.41–2.48 (m, 2, Ar—CH$_2$—CH$_2$), 2.52–2.62 (m, 2, CH$_2$—CHOH), 2.75–2.78 (m, 4, Ar—CH$_2$—CH$_2$—CH$_2$), 2.83–2.92 (m, 2, CH$_2$—CH$_2$—CHOH), 3.01–3.06 (d, 2, N—CH$_2$—CHN, J=10.0 Hz), 3.38–3.56 (m, 3, Ar—CH$_2$—N+CH—N), 3.85 (s, 1, CH—OH), 7.02–7.31 (m, 5, arom.), 7.44–7.48 (d, 1, arom., J=7.8 Hz), 7.58–7.62 (d, 1, arom., J=7.9 Hz), 7.68 (s, 1, arom.).

1'-(1-(2-Iodobenzyl)-4-hydroxypiperidin-3-yl)-3,4-dihydrospiro[naphthalene-1(2H),4'-piperidine] (13c)

A mixture of the dihydrochloride of 21c (250 mg, 0.67 mmol), DMF (10 mL), potassium carbonate (463 mg, 3.35 mmol) and 2-iodobenzyl chloride (1.00 mmol), 254 mg) was stirred at room temperature for 18 h. Water (25 mL) and dichloromethane (2×25 mL) were added and the organic layer was extracted, washed with brine (25 mL), dried (Na$_2$SO$_4$) and concentrated. The crude product was purified by chromatography (silica gel, hexanes/ethyl acetate, 50/50) to afford 13c as a yellow oil. The latter was converted to the corresponding hydrochloride in satd HCl/ether and recrystallized twice from 50% i-PrOH-hexanes to yield 0.20g (33%) of 13c; mp 258.8° C. $^1$H NMR (CDCl$_3$) δ1.50–2.21 (2 m, 8, 2N—CH$_2$—CH$_2$), 2.45–2.57 (m, 2H, Ar—CH$_2$—CH$_2$, J=10.2 Hz), 2.60–2.76 (m, 2, CH$_2$—CHOH), 2.84 (m, 4, Ar—CH$_2$—CH$_2$—CH$_2$), 2.88–3.00 (t, 2, CH$_2$—CH$_2$—CHOH, J=11.2 Hz), 3.09–3.13 (d, 2, N—CH$_2$—CHN, J=8.7 Hz), 3.50–3.64 (m, 3, Ar—CH$_2$—N+CH—N), 3.85 (s, 1, CH—OH), 4.67 (s, 1, OH), 6.96–7.49 (m, 8H, arom.), 7.83–7.87 (d, 1H, arom., J=6.8 Hz).

1'-(1-(4-fluorobenzyl)-4-hydroxypiperidin-3-yl)-3,4-dihydrospiro[naphthalene-1(2H),4'-piperidine] (13f)

Procedure E

Yield, 13%; mp 232.4° C.; $^1$H NMR (CDCl$_3$) δ1.50–2.10 (m, 8, 2 N—CH$_2$—CH$_2$), 3.47–2.52 (m, 2, Ar—CH$_2$—CH$_2$), 2.59–2.64 (dt, 2, CH$_2$—CHOH, J=2.1 Hz, J'=10.1 Hz), 2.68–2.78 (m, 4, Ar—CH$_2$—CH$_2$—CH$_2$), 2.87–2.99 (t, 2, CH$_2$—CH$_2$—CHOH, J=11.0 Hz), 3.05–3.10 (d, 2, N—CH$_2$—CHN, J=10.2 Hz), 3.76–3.80 (m, 3, Ar—CH$_2$—N+CH—N), 3.90 (s, 1, CH—OH), 4.55 (s, 1, OH), 6.75–7.49 (m, 8H, arom.).

Procedure G

1'-(1-(4-Iodobenzyl)-4-hydroxypiperidin-3-yl)-3,4-dihydrospiro[naphthalene-1(2H),4'-piperidine] (13e)

A mixture of the hydrochloride of 21c (250 mg, 0.67 mmol), potassium carbonate (463 mg, 3.35 mmol) and 4-iodobenzyl chloride (298 mg, 1.00 mmol) in absolute ethanol (25 mL) was refluxed for 16 h. When the mixture had cooled, salts were filtered off and the volatiles were removed under reduced pressure. The residue was dissolved in ethyl acetate (25 mL) and the solution was successively washed with water (25 mL) and brine (25 mL). The organic layer was then dried (Na$_2$SO$_4$) and concentrated. The product was purified by chromatography (silica gel, hexanes/ ethyl acetate: 50/50) and (13e) was obtained as a colorless oil (226 mg, 52%). The hydrochloride was prepared in a satd HCl/ether soln and recrystallized twice from 50% isopropyl alcohol-hexanes to yield a yellow powder; mp 256.3° C.; $^1$H NMR (CDCl$_3$) δ1.56–2.18 (2 m, 8, 2 N—CH$_2$—CH$_2$), 2.40–2.45 (d, 2H, Ar—CH$_2$—CH$_2$, J=10.1 Hz), 2.51–2.60 (m, 2, CH$_2$—CHOH), 2.72–2.78 (m, 4, Ar—CH$_2$-CH$_2$—CH$_2$), 2.84–2.97 (t, 2, N—CH$_2$—CH$_2$—CHOH, J=11.9 Hz), 3.05–3.50 (d, 2, CHN—CH$_2$—N, J=10.4 Hz), 3.40–3.55 (m, 4, CH—OH+Ar—CH$_2$—N+CHN), 3.81 (s, 1, OH), 7.22–7.02 (m, 4, arom.), 7.42–7.46 (d, 2, arom., J=7.7 Hz), 7.63–7.67 (d, 2, arom., J=8.2 Hz).

1'-(2-Hydroxy-1,2,3,4-tetrahydronaphth-3-yl)-spiro[2-bromo-1H-indene-1,4'-piperidine]Hydrochloride (14)

Compound 24 was prepared from 2-bromo-1H-indene by Procedure H, below, and purified by radial flow chromatography in silica gel (hexanes,94:acetone,5:Et$_3$N, 1) to yield 3.0 g (57%) of a golden yellow syrup; $^1$H NMR (CDCl$_3$) δ1.24–1.29 (d,2,piperidyl β-H$_{eq}$), 1.44–1.54 (s,9,t-butoxy), 2.04–2.12 (m,2,piperidyl β-H$_{ax}$), 3.45–3.60 (m,2, piperidyl α-H$_{ax}$), 4.21–4.35 (br s, piperidyl α-H$_{eq}$), 6.85 (s,1, indenyl C3-H), 7.13–7.31 (m,indenyl C4-,C5- fr C6-H), 7.80 (d,1, indenyl C7-H). Compound 24 (2.8g, 7.85 mmol was converted to 25 in as described for 21a above. This product was added to a soln of 1,4-dihydronaphthalene oxide, prepared from the corresponding bromohydrin (9.0 mmol as described in Procedure B above, in EtOH (10 mL) and Et$_3$N (10 mL. The resulting mixture was refluxed for 40 h, cooled to r.t. and conc in vacuo. The residue partitioned between CH$_2$Cl$_2$ (50 mL) and said NaHCO$_3$ (30 mL). After separation of the phases, the aq. layer was re-extracted with CH$_2$Cl$_2$ (2×30 mL). The combined organic extracts were dried over anhyd. Na$_2$SO$_4$ and conc to a residue. The latter was subjected to radial flow chromatography on silica gel (hexanes,79:acetone,20:Et$_3$N, 1) to provide 1.92 g (60%) of 14 as a syrup. $^1$H NMR (CDCl$_3$) δ1.43 (d, 2, piperidyl β-H$_{eq}$, J=10.5 Hz), 2.13–2.32 (m, 2, piperidyl β-H$_{ax}$), 2.81–3.49 (m, 9, tetrahydronaphthyl C1-H, C3-H, C4-H & piperidyl α-H), 3.96 (m, 1, CHOH), 6.88 (s, 1, indenyl C3-H), 7.02–7.97 (m, 7, aryl), 7.81 (d, 1, indenyl C7-H, J=7.2 Hz). The corresponding hydrochloride was obtained in cold methanolic HCl and recrystallized from i-PrOH as an off-white solid; mp 278°–281° C.

1'-(2-Hydroxy-1,2,3,4-tetrahydronaphth-3-yl)-spiro[4-bromo-1H-indene-1,4'-piperidine]Hydrochloride (15)

The reaction of 7-bromo-1H-indene (3.50 g, 17.94 mmol, with LiN[Si(CH$_3$)$_3$]$_2$ and bis(2-chloroethyl)-tert-butyl carbamate (Procedure H) yielded a mixture of two products (5.85g, 90%) in a ratio of 85:15, respectively, as revealed by HPLC (silica gel, 2% acetone-hexanes). Deprotection (see 21a), subsequent neutralization and extraction into EtOAc yielded, after concentration, 2.2 g (46%) of the crude free base. Trituration of this residue with CH$_2$Cl$_2$ yielded 27 as a white solid which was collected by filtration, washed with CH$_2$Cl$_2$ and dried at 50° C. in vacuo; mp 310°–315° C. (sinters); $^1$H NMR (DMSO$_{d6}$) δ1.30 (d, 2, piperidyl α-H$_{eq}$, J=13.5 Hz), 2.38 (dt, 2, piperidyl δ-H$_{ax}$, J=12.9 Hz, J'=4.8 Hz), 3.21 (dt, 2, piperidyl α-H$_{ax}$, J=13.4 Hz, J'=2.4 Hz), 3.35 (d, 2, piperidyl α-H$_{eq}$, J=11.1 Hz), 6.78 (d, 1, indenyl C2-H, J=6.0 Hz), 7.14 (t, 1, indenyl C6-H, J=8.4 Hz), 7.26 (d, 1, indenyl C2-H, J=6.0 Hz), 7.29 (d, 1, indenyl C5-H, J=6.0 Hz), 7.40 (d, 1, indenyl C7-H, J=8.4 Hz). A soln of 1M Et$_3$Al in toluene (0.65 mL) was added dropwise at room temperature, under N$_2$, to a stirring suspension of 27 (0.30 g, 1.13 mmol) in CH$_2$Cl$_2$ (13 mL).

Complete dissolution occurred at the end of the addition. The resulting soln was stirred at r.t. for 40 min at which time a soln of 1,4-dihydronaphthalene oxide in $CH_2Cl_2$ (5 mL), prepared from the corresponding bromohydrin (1.35 mmol) as described in Procedure B above, was added dropwise over 5 min. Stirring was contd for 21 h. The reaction was quenched by dropwise addition of 4N NaOH (20 mL). The resulting mixture was stirred vigorously for 2 h, diluted with $H_2O$ (25 mL) and extracted with $CH_2Cl_2$ (3×30 mL). The combined organic extracts were dried over $NaSO_4$ and conc to a tan solid which was purified by radial flow chromatography on silica gel (hexanes,79:acetone,20:$Et_3N$,1) to yield an off-white solid (0.30g, 65%); mp 265°–267° C.; $^1H$ NMR ($CDCl_3$) $\delta 1.45$ (d, 2, piperidyl $\beta$-$H_{eq}$, J=12.9 Hz), 2.10–2.28 (m, 2, piperidyl $\alpha$-$H_{ax}$) 2.65 (t, 1, piperidyl $\alpha$-$H_{ax}$, J=11.4 Hz), 2.81–3.11 (m, 7, tetrahydronaphthyl C1-H, C4-H & piperidyl), 3.35 (dd, 1, piperidyl a-$H_{eq}$, J=16.1 Hz, J'=5.7 Hz), 3.93 (m, 1, CHOH), 6.87 (d, 1, indenyl C2-H, J=5.7 Hz), 6.96 (d, 1, indenyl C3-H, J=5.7 Hz), 7.12 (m, 5, aryl), 7.31 (d, 1, indenyl C5-H, J=7.4 Hz), 7.38 (d, 1, indenyl C7-H, J=7.9 Hz).

Procedure H

5-Bromo-1'-tert-butoxycarbonylspiro[1H-indene-1,4'-piperidine] (29) and
6-Bromo-1'-tert-butoxycarbonyl spiro[1H-indene-1,4'-piperidine] (30)

A soln of 1M LiN[(Si $CH_3)_3]_2$ in THF (45 mL) was added dropwise over 20 min, under $N_2$, to a cooled (icebath) stirring soln of 5-bromo-1H-indene (3.90 g, 20.0 mmol) in dry THF (15 mL). Following the addition, stirring was contd at 4° C. for 45 min. The dark soln was then transferred via cannula to a precooled (icebath) solution of N,N-bis(2-chloroethyl)-tert-butyl carbamate (4.84 g, 20.0 mmol in dry THF (15 mL). The resulting solution was stirred at 4° C. for 2 h and then at r.t. for 18 h. The dark purple mixture was conc in vacuo, and the residue was triturated with a small volume of 20% acetone-hexanes and applied into a short silica gel column. The latter was eluted with the same solvent (300 mL). The eluent was concentrated to yield 6.45 g (88%) of the crude mixture of 29and 30 which was considered pure enough for use without further purification. However; a small fraction of this material was purified by radial flow chromatography on silica gel (hexanes, 89:acetone, 10:$Et_3N$, 1) to provide an orange colored syrup; $^1H$ NMR ($CDCl_3$) $\delta 1.30$ (d, 2, piperidyl $\beta$-$H_{eq}$, J=16.8 Hz), 1.50 (s, 9, t-butoxy), 1.96 (dt, 2, piperidyl $\beta$-$H_{ax}$, J=12.3 Hz, J'=4.6 Hz), 3.09 (t, 2, piperidyl $\alpha$-$H_{ax}$, J=13.0 Hz), 4.17 (b-d, 2, piperidyl $\alpha$-$H_{eq}$, J=13.0 Hz), 6.71 (d, 1, indenyl C2-H, J=5.78 Hz), 6.85 (m, 1, indenyl C3-H), 7.14–7.45 (m, 3, aryl). Anal. ($C_{18}H_{22}BrNO_2$) C,H,N.

1'-(2-Hydroxy-1,
2,3,4-tetrahydronaphth-3-yl)-spiro[5-bromo-1H-indene-1,4'-piperidine]Hydrochloride (16) and
1'-(2-Hydroxy-1,2,3,4-tetrahydronaphth-3-yl)spiro[6-bromo-1H-indene-1,4'-piperidine]Hydrochloride (17)

HCl(g) was vigorously bubbled through a cooled (icebath) solution of 29 and 30 (6.20 g, 17.0 mmol) in EtOAc (100 mL). The resulting soln was stirred at 4° C. for an additional 45 min and conc in vacuo to a brown solid. The latter was triturated with $Et_2O$, filtered, washed with $Et_2O$ and dried to afford 4.12 (80%) of a mixture of isomeric bromospiro[1H-indene- 1,4-piperidine) hydrochlorides. A fraction of this mixture (2.0 g, 6.65 mmol) was added to a soln of 1,4-dihydronaphthalene oxide, prepared from corresponding bromohydrin (1.61 g, 7.1 mmol), in EtOH (50 mL) and $Et_3N$ (20 mL). The mixture was refluxed for 72 h, cooled to r.t. and conc in vacuo to a syrup. The latter was diluted with $CH_2Cl_2$ and the soln was washed with satd $NaHCO_3$ (40 mL). The aq. layer was re-extracted with $CH_2Cl_2$ (40 mL) and set aside. The combined organic extracts were dried over $Na_2SO_4$ and conc to a residue. Radial flow chromatographic separation (hexanes, 89:acetone,10:$Et_3N$,1) yielded a small fraction of starting material (0.30 g, 17%) and two products. The more mobile product, 16, was obtained as a white powder (0.2 g, 10%) which was converted to the hydrochloride in MeOH and recrystallized from isopropyl alcohol; mp 259°–263° C.; $^1H$ NMR ($CDCl_3$) $\delta 1.44$ (d, 2, piperidyl$\beta H_{eq}$, J=12.8 Hz), 2.08–2.30 (m, 2, piperidyl $\beta H_{ax}$, ), 2.64 (t, 1, piperidyl $\alpha$-$H_{ax}$, J=9.8 Hz), 2.59–3.12 (m, 7, tetrahydronaphthyl C1-H, C4-H & piperidyl), 3.35 (dd, 1, piperidyl $\alpha H$-$_{eq}$, J=16 Hz, J'=5.8 Hz), 3.94 (m, 1, CHOH), 6.72 (d, 1, indenyl C2-H, J=5.6 Hz), 6.90 (d, 1, indenyl C3-H, J=5.7 Hz), 7.14 (s, 4, tetrahydronaphthyl C5-H, C6-H, C7-H, C8-H), 7.18 (d, 1, indenyl C7-H, J=8.1 Hz), 7.38 (dd, 1, indenyl C6-H, J=7.9 Hz, J'=1.6 Hz), 7.53 (d, 1, indenyl C4-H, J=7.6 Hz).

The less mobile product, 17, was also obtained in 10% yield, and converted to the hydrochloride in a similar manner; mp 269 –270° C. $^1H$ NMR ($CDCl_3$) $\delta 1.43$ (d, 2, piperidyl $\beta$-$H_{eq}$, J=13.2 Hz), 2.16 (m, 2, piperidyl $\beta$-$H_{ax}$), 2.64 (t, 1, piperidyl $\alpha$-$H_{ax}$, J=9.8 Hz), 2.79–3.12 (m, 7, tetrahydronaphthyl C1-H, C4-H & piperidyl), 2.94–3.40 (dd, 1, piperidyl $\alpha$-$H_{eq}$, J=16.1 Hz, J'=5.7 Hz), 3.94 (m, 1, CHOH), 6.72 (d, 1, indenyl C2-H, J=5.7 Hz), 6.92 (d, 1, indenyl C3-H, J=5.6 Hz), 7.14 (s, 5, tetrahydronaphthyl C5-H, C6-H, C7-H, C8-H), 7.27 (d, 1, indenyl C4-H, J=6.6 Hz), 7.36 (dd, 1, indenyl C5-H, J=7.9 Hz, J'=1.7 Hz), 7.48 (d, 1, indenyl C7-H, J=1.6 Hz).

TABLE 1

| | Pharmacological Activity of Spirovesamicols in Male Wistar Rats Dose (umol/Kg) | | | | | | | | | |
|---|---|---|---|---|---|---|---|---|---|---|
| Compound | 1 | 5 | 10 | 12.5 | 20 | 22.5 | 25 | 45 | 50 | 125 |
| 15 | | | | | – | NR | | | + | |
| 14 | | | | | + | | $LD_{100}$ | | $LD_{100}$ | |
| 13d | | | | | | | NR | | S | $LD_{100}$ |
| 11a | | | | + | | ++ | | $LD_{100}$ | | |
| 11b | | ++ | $LD_{100}$ | $LD_{100}$ | | | $LD_{100}$ | | | |

TABLE 2

Pharmacological Activity of Spirovesamicols in Male Swiss Webster Mice
Dose (umol/Kg)

| Compound | 1.25 | 2.5 | 5.0 | 6.25 | 10 | 12.5 | 20 | 25 | 40 | 50 | 100 |
|---|---|---|---|---|---|---|---|---|---|---|---|
| 11a |  |  |  | NR |  | + | $LD_{40}$ |  |  | $LD_{60}$ | $LD_{100}$ |
| 11b | + | $LD_{20}$ | $LD_{20}$ |  | $LD_{40}$ |  | $LD_{60}$ | $LD_{100}$ |  |  |  |

Legend for Table 1 and 2

Rats and mice were injected intraperitoneally with solutions of the compounds in aqueous EtOH (or aqueous DMSO). The animals were observed for signs of anticholinergic activity: spasms, respiratory distress and paralysis. At lethal doses, death generally occurred within 20 minutes following the injection. $LD_{20}$ lethal dose for 20% of animals tested; $LD_{40}$, lethal dose for 40%; $LD_{60}$, lethal dose for 60%; $L_{100}$, lethal dose for all animals; NR, no visible pharmacologic reaction; S, sluggishness and reduced locomotor activity; +, mild symptoms of anticholinergic activity; ++, severe signs of anticholinergic activity.

TABLE 3

Inhibitory potency of Spirovesamicols

| Compound | Ki (nM) |
|---|---|
| 1 | 1.0 |
| 11a | 0.622 ± 0.082 |
| 11b | 0.121 ± 0.032 |
| 11c | 0.798 ± 0.187 |
| 11d | 0.264 ± 0.078 |
| 11f | 0.248 ± 0.025 |
| 13a | 24.25 ± 5.71 |
| 13b | 18.36 ± 14.03 |
| 13c | 5.80 ± 1.70 |
| 13d | 0.082 ± 0.020 |
| 13f | 2.60 ± 0.90 |
| 14 | 0.038 ± 0.006 |
| 15 | 0.212 ± 0.063 |
| 16 | 1.40 ± 0.30 |
| 17 | 0.271 ± 0.056 |

TABLE 4

Elemental Analyses

| Compound | Formula | C Calc Found | H Calc Found | N Calc Found |
|---|---|---|---|---|
| 11a | $C_{19}H_{25}NO \cdot HCL \cdot \frac{1}{2}H_2O$ | 69.39 / 68.89 | 8.28 / 8.20 | 4.26 / 4.13 |
| 11b | $C_{23}H_{25}NO \cdot HCL \cdot \frac{1}{2}H_2O$ | 73.29 / 73.34 | 6.95 / 7.29 | 3.72 / 3.44 |
| 11c | $C_{25}H_{29}IN_2O - 2HCl \cdot \frac{1}{4}H_2O$ | 51.96 / 51.93 | 5.50 / 5.79 | 4.85 / 4.80 |
| 11d | $C_{25}H_{29}INO - 2HCl \cdot \frac{1}{4}H_2O$ | 51.55 / 51.45 | 5.53 / 5.89 | 4.81 / 4.57 |
| 11e | $C_{25}H_{29}IN_2O \cdot 2HCl \cdot \frac{3}{4}H_2O$ | 51.17 / 50.89 | 5.58 / 5.69 | 4.77 / 4.80 |
| 11f | $C_{25}H_{29}FNO \cdot 2C_2H_2O_4$ | 60.81 / 62.52 | 5.81 / 6.18 | 4.89 / 5.32 |
| 12a | $C_{19}H_{27}NO \cdot HCl \cdot \frac{1}{4}H_2O$ | 70.04 / 69.86 | 8.73 / 8.72 | 4.27 / 4.28 |
| 12b | $C_{23}H_{27}NO \cdot HCl \cdot \frac{1}{2}H_2O$ | 69.28 / 69.59 | 7.42 / 7.87 | 3.60 / 3.53 |
| 12c | $C_{25}H_{31}IN_2O \cdot 2HCl \cdot \frac{1}{2}H_2O$ | 51.38 / 51.24 | 5.86 / 5.72 | 4.80 / 4.77 |
| 12d | $C_{25}H_{31}IN_2O \cdot 2HCl \cdot \frac{1}{2}H_2O$ | 51.38 / 51.27 | 5.86 / 5.82 | 4.80 / 4.60 |
| 12e | $C_{25}H_{31}IN_2O \cdot 2HCl \cdot \frac{1}{2}H_2O$ | 51.38 / 51.04 | 5.86 / 5.76 | 4.80 / 4.70 |
| 12f | $C_{25}H_{31}FN_2O \cdot 2C_2H_2O_4$ | 60.61 / 61.37 | 6.14 / 6.53 | 4.88 / 5.01 |
| 13a | $C_{20}H_{29}NO \cdot HCl$ | 71.51 / 71.35 | 9.00 / 9.05 | 4.17 / 4.13 |
| 13b | $C_{24}H_{29}NO \cdot HCl$ | 72.52 / 72.52 | 7.99 / 7.98 | 3.52 / 3.53 |
| 13c | $C_{26}H_{33}IN_2O \cdot 2HCl \cdot H_2O$ | 51.41 / 51.63 | 6.14 / 6.02 | 4.61 / 4.62 |
| 13d | $C_{26}H_{33}IN_2O$ | 60.47 / 60.35 | 6.44 / 6.47 | 5.42 / 5.36 |
| 13e | $C_{26}H_{33}IN_2O \cdot 2HCl \cdot H_2O$ | 51.41 / 51.16 | 6.14 / 6.12 | 4.61 / 4.59 |
| 13f | $C_{26}H_{33}FN_2O \cdot 2HCl$ | 64.86 / 59.40 | 7.33 / 7.61 | 5.82 / 5.36 |
| 20a | $C_{23}H_{32}N_2O_3$ | 71.84 / 71.60 | 8.39 / 8.53 | 7.29 / 7.22 |
| 20b | $C_{23}H_{34}N_2O_3$ | 71.46 / 70.47 | 8.87 / 8.84 | 7.25 / 7.21 |
| (dl)20c | $C_{24}H_{36}N_2O_3$ | 71.96 / 71.92 | 9.06 / 9.09 | 6.79 / 7.02 |
| (+)-20c | $C_{24}H_{36}N_2O_3$ | 71.96 / 71.93 | 9.06 / 9.10 | 6.79 / 6.87 |
| (−)-20c | $C_{24}H_{36}N_2O_3$ | 71.96 / 71.78 | 9.06 / 9.08 | 6.79 / 6.92 |
| 19c | $C_{24}H_{36}N_2O_3$ | 71.96 / 71.77 | 9.06 / 9.07 | 6.79 / 6.90 |
| 29 + 30 | $C_{18}H_{22}BrNO_2$ | 59.35 / 59.04 | 6.09 / 6.16 | 3.85 / 3.86 |
| 14 | $C_{23}H_{24}BrClNO \cdot HCl$ | 61.83 / 61.58 | 5.64 / 5.60 | 3.13 / 3.12 |
| 15 | $C_{23}H_{24}BrClNO \cdot HCl \cdot H_2O$ | 59.43 / 58.00 | 5.64 / 5.66 | 3.01 / 3.00 |
| 16 | $C_{23}H_{24}BrClNO \cdot HCl$ | 61.83 / 61.70 | 5.64 / 5.68 | 3.13 / 3.13 |
| 17 | $C_{23}H_{24}BrClNO \cdot HCl$ | 61.83 / 61.77 | 5.64 / 5.66 | 3.13 / 3.13 |

Methods for the introduction of aryl and heteroaryl groups into the C2 and C3 positions of indene have been reported (Greifenstein et al., 1981). Those of ordinary skill in the art may make these variations readily.

Figure 5:
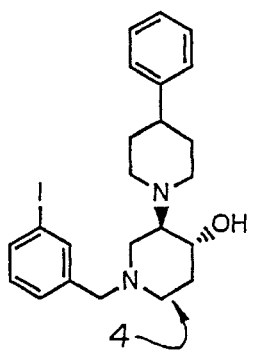
Figure 6:
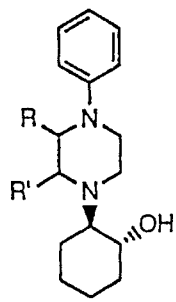
Figure 7:
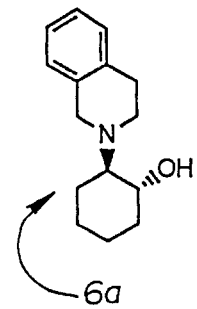
Figure 8:
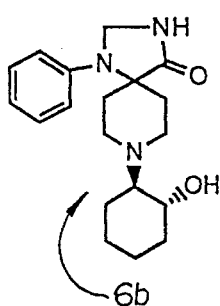
Figure 9:
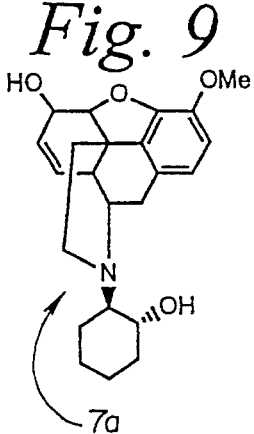
Figure 10:
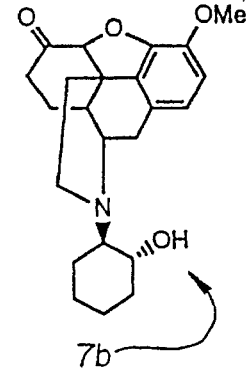
Figure 17:
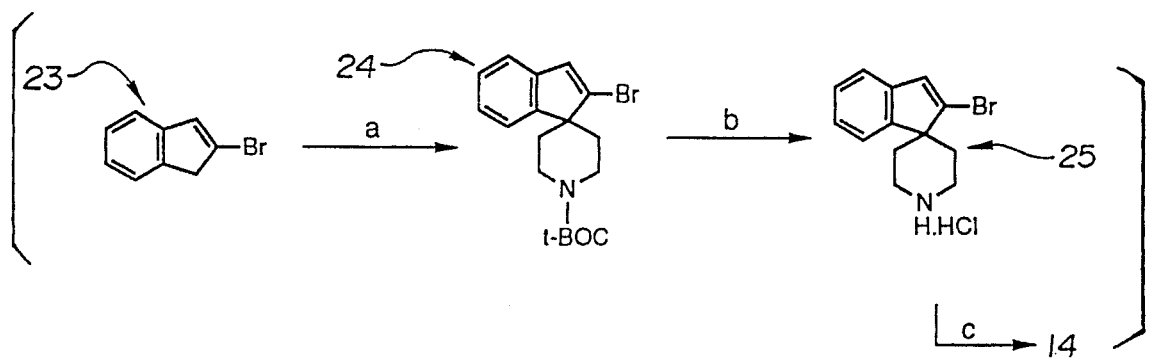
FIGS. 17–19 shows Scheme 2, the synthesis of brominated spirovesamicols.
Figure 18:
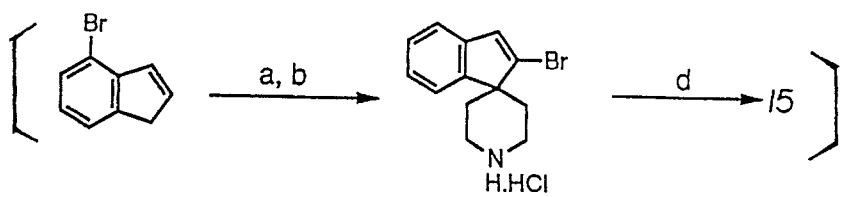
Figure 19:
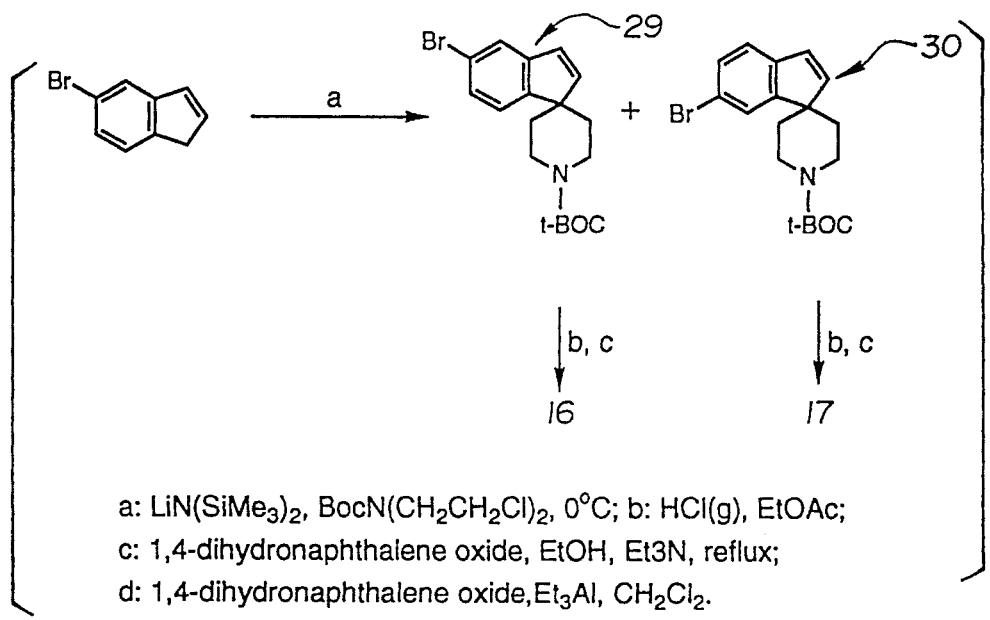
Figure 20:
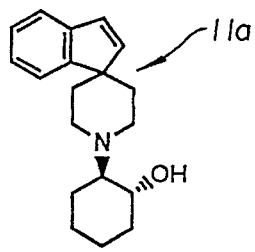
FIGS. 20–32 shows spirovesamicols of the invention.
Figure 21:
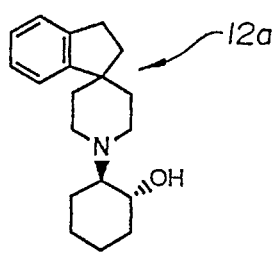
Figure 22:
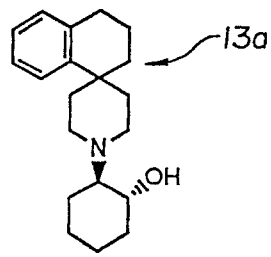
Figure 23:
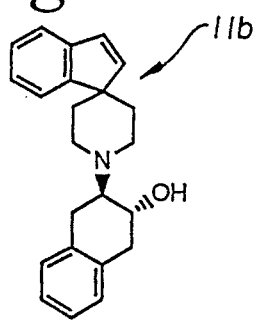
Figure 24:
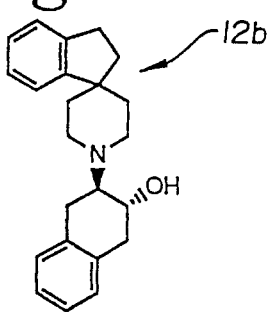
Figure 25:
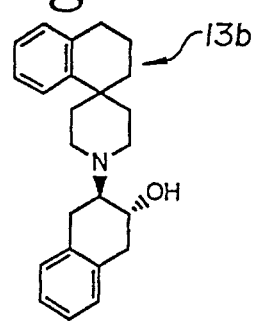
Figure 26:
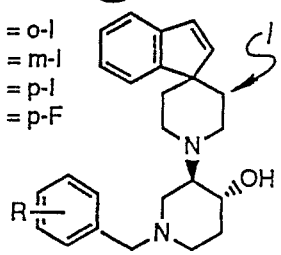
Figure 27:
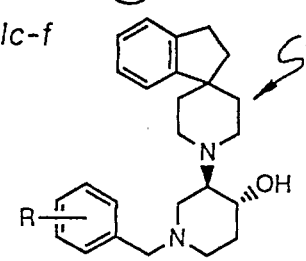
Figure 28:
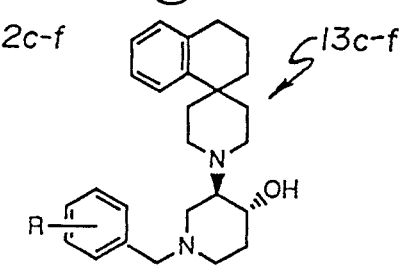
Figure 29:
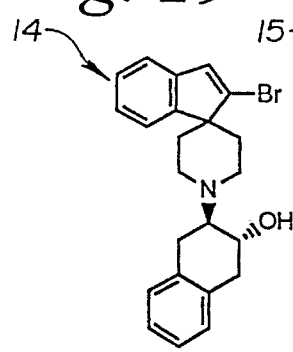
Figure 30:
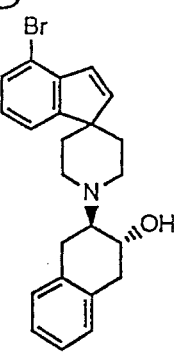
Figure 31:
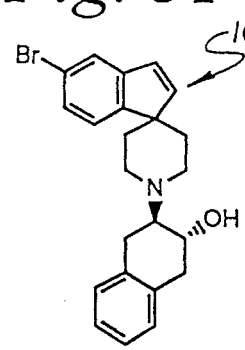
Figure 32:
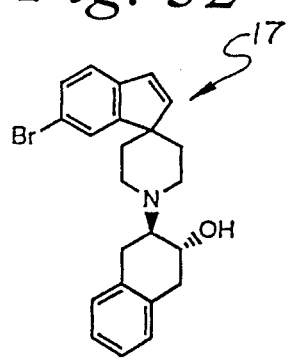

FIG. 5 shows the potency of vesamicol analogs at human sigma receptors. Each analog was incubated in the presence of 5 nM (+)-[$^3$H]PPP in 10 mM Tris buffer for 1 hr at 25° C. Nonspecific binding was determined in the presence of 100 μM (dl)-pentazocine. The fraction of sites occupied (inhibited) by each analog at a dose of 1 μM is shown. Each point represents a mean of three determinations. The Y axis is % Sites Occupied.

USES

These compounds are useful for many applications. They may be used in a method for noninvasively mapping cholinergic innervation in a living brain, which comprises injecting a subject with an effective amount of a radioiodinated spirovesamicol or other radiolabeled compound based on a spirovesamicol with a chelating sidechain complexed with a radionuclide such as Tc-99 m, Re-18b and Ga-68 which emits gamma or positron radiation capable of tissue penetration and subsequent external detection by a photoscanning device; and subsequently scanning with said photoscanning device to visualize cholinergic innervation.

The spirovesamicols may be used in a method for photoaffinity labelling of the vesamicol protein, which comprises treatment of tissues with an effective amount of photoaffinity label including spirovesamicol wherein the sidechain is azidoaryl, azidoarylalkyl, azidoaroyl, azidoheteroaryl or azidoheteroaroyl; and inducing chemical bond formation between the azido group and the vesamicol receptor by exposure to light.

The spirovesamicols may be used in a method for visualization of cholinergic innervation in the mammalian brain which comprises the application of an effective amount of a spirovesamicol including a sidechain containing a fluorescent or visible dye or chromophore; and subsequent visualization of the tissue with light.

The spirovesamicols may be used in a method for blocking cholinergic neurotransmission in mammals or other animals which involves the application of a spirovesamicol composition as an active ingredient including a sidechain that is alkyl, arylalkyl, cycloalkyl, heteroalkyl or acyl. Examples include uses with rhinitis and operoneuron disease.

The spirovesamicols may be used in a method for noninvasive detection of cholinergic innervation in a living brain, which comprises injecting a subject with an effective amount of a magnetic resonance contrast agent comprising a spirovesamicol with a chelating sidechain complexed with a paramagnetic cation capable of enhancing contrast in magnetic resonance imaging; and subsequently scanning with a magnetic resonance imager.

The spirovesamicols may be used in a method for autoradiographic visualization of the distribution of cholinergic pathways in animal tissue which comprises introduction by injection to a subject or incubation of a tissue sample with a radiolabelled spirovesamicol with a sidechain containing a radiolabel; and subsequent visualization by autoradiography.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A compound capable of binding to a vesamicol receptor selected from:

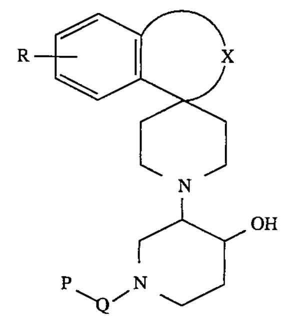

wherein

X is —CH=CH—, —$CH_2CH_2$—, $(CH_2)_3$, —CY=CZ—, —CHY—CHZ—;

Y is H, halogen;

Z is H, halogen;

R is H or halogen;

P is phenyl, substituted phenyl; and

Q is an alkylene chain having between 0 and 4 carbons.

* * * * *